US010835264B2

(12) United States Patent
Boileau et al.

(10) Patent No.: US 10,835,264 B2
(45) Date of Patent: Nov. 17, 2020

(54) DRILL GUIDE

(71) Applicant: Smith & Nephew, Inc., Memphis, TN (US)

(72) Inventors: Pascal Boileau, Nice (FR); Dirk Wunderle, Zurich (CH); Stephen Anthony Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 269 days.

(21) Appl. No.: 16/180,365

(22) Filed: Nov. 5, 2018

(65) Prior Publication Data

US 2019/0069912 A1    Mar. 7, 2019

Related U.S. Application Data

(62) Division of application No. 14/622,296, filed on Feb. 13, 2015, now Pat. No. 10,123,813.

(60) Provisional application No. 61/940,733, filed on Feb. 17, 2014.

(51) Int. Cl.
*A61B 17/00* (2006.01)
*A61B 17/17* (2006.01)

(52) U.S. Cl.
CPC ...... *A61B 17/1739* (2013.01); *A61B 17/1796* (2013.01); *A61B 17/1778* (2016.11)

(58) Field of Classification Search
CPC combination set(s) only.
See application file for complete search history.

(56) References Cited

U.S. PATENT DOCUMENTS

2012/0123417 A1 * 5/2012 Smith ............... A61B 17/1714
606/80

* cited by examiner

*Primary Examiner* — Sameh R Boles
(74) *Attorney, Agent, or Firm* — Burns & Levinson, LLP; Joseph M. Maraia (57) ABSTRACT

A drill guide includes a body, a stabilizing member, a tubular guide sleeve, and an engagement member. The body includes a first channel aligned with a longitudinal axis and a second channel transverse to the longitudinal axis. The first channel is dimensioned to receive the sleeve, while the second channel is dimensioned to receive an engagement member. The engagement member is adapted to move within the second channel between an engaged position, where the engagement member inhibits proximal motion of the sleeve, and a second position, where motion of the sleeve is not inhibited. An alignment member is further mounted to the distal end of the sleeve that includes a distally extending member, spaced from the sleeve. In use, the distally extending member may be employed to exert a force upon a bone or other tissue lateral to the longitudinal axis for improved positioning of the bone or tissue.

10 Claims, 13 Drawing Sheets

DRILL GUIDE

CROSS-REFERENCE TO RELATED APPLICATION(S)

This application is a division of U.S. patent application Ser. No. 14/622,296, filed on Feb. 13, 2015, entitled DRILL GUIDE, which in turn claims the benefit of priority of U.S. Provisional Patent Application No. 61/940,733, filed on Feb. 17, 2014, the entirety of which is hereby incorporated by reference.

BACKGROUND

Joint and ligament injuries are common. One type of such injuries includes acromioclavicular joint disruptions. In treating these joint injuries, it has been common to utilize woven polyester slings or surgical screws. The goal of any such treatment is to re-approximate bones, tendons and ligaments back to their anatomical locations to facilitate the healing process.

SUMMARY

In an embodiment of the disclosure, a drill guide is provided. The drill guide includes a tubular guide sleeve extending along a longitudinal axis of the drill guide between a proximal end and a distal end and a drill guide body including a proximally-facing surface, a distally-facing surface, and a plurality of lateral surfaces extending there-between. The drill guide body further includes: a first channel extending through the guide body between the proximal and distal guide body surfaces and aligned with the longitudinal axis, the first channel dimensioned to receive the tubular sleeve; and a second channel extending through at least a portion of the guide body and a lateral surface of the guide body transverse to the longitudinal axis, the second channel intersecting the first channel. The drill guide further includes an alignment member attached to the distal end of the sleeve, where the alignment member includes a distally facing surface and an elongate locating member extending distally from the distally facing surface of the alignment member, where the locating member is laterally spaced from the longitudinal axis and where a distal end of the locating member extends distally beyond the distal tip of the sleeve. The drill guide additionally includes an engagement member dimensioned for placement within the second channel, where the engagement member includes a through-passageway oriented parallel to the first channel when the engagement member is positioned within the second channel, the passageway dimensioned for receipt of a portion of the sleeve therein. The engagement member is further adapted to move within the second channel between an engaged position and a disengaged position, where the engagement member inhibits proximal movement of the sleeve in the engaged position, and where the engagement member does not inhibit proximal movement of the sleeve in the disengaged position.

Embodiments of the drill guide may further include one or more of the following, in any combination.

In an embodiment of the drill guide, the second passageway is approximately perpendicular to the first passageway.

In an embodiment, the drill guide further includes a ratchet mechanism. The ratchet mechanism includes a pawl mounted to the engagement member and a plurality of teeth mounted to the sleeve, where the pawl engages the plurality of teeth in the engaged position of the engagement member to inhibit proximal motion of the sleeve.

In an embodiment, the drill guide further includes a biasing mechanism positioned within the second channel, where the biasing mechanism biases the engagement member in the engaged position.

In an embodiment, the drill guide further includes a stabilizing member. The stabilizing member includes a first elongated portion extending distally from the guide body, where a distal end of the first portion is positioned distally with respect to the distal end of the sleeve, and a second elongated portion extending from the distal end of the first portion and transversely with respect to the longitudinal axis and where the second portion of the stabilizing member intersects the longitudinal axis.

In an embodiment of the drill guide, the locating member extends approximately parallel to the sleeve.

In an embodiment of the disclosure, a method of joint repair is provided. The method includes securing a drill guide body with respect to a patient's anatomy. The drill guide body includes a proximally-facing surface, a distally-facing surface, and a plurality of lateral surfaces extending there-between. The drill guide body further includes: a first channel extending through the guide body between the proximal and distal guide body surfaces and aligned with the longitudinal axis, the first channel dimensioned to receive a tubular drill guide sleeve, and a second channel extending through at least a portion of the guide body and a lateral surface of the guide body transverse to the longitudinal axis, the second channel intersecting the first channel. The drill guide also includes an engagement member dimensioned for placement within the second channel, the engagement member including a through-passageway oriented parallel to the first channel when the engagement member is positioned within the second channel, the passageway dimensioned for receipt of a portion of the drill guide sleeve therein. The engagement member is adapted to move within the second channel between an engaged position and a disengaged position. The engagement member inhibits proximal movement of the sleeve in the engaged position and the engagement member does not inhibit proximal movement of the sleeve in the disengaged position. The method also includes positioning the drill guide sleeve within the first channel. The drill guide sleeve includes a tubular sleeve body extending between a proximal end and a distal end; and an alignment member attached to the distal end of the sleeve body. The alignment member includes a distally facing surface and an elongate locating member extending distally from the distally facing surface of the alignment member, where the locating member is laterally spaced from the longitudinal axis and where a distal end of the locating member extends distally beyond the distal tip of the sleeve body. The method also includes positioning the drill sleeve guide with respect to a first bone, including sliding the drill guide sleeve distally such that the distal end of the sleeve contacts a proximally-facing surface of the first bone, where at least a portion of the sleeve remains within the first channel of the guide body and where at least a portion of the locating member contacts a laterally-facing surface of the first bone.

Embodiments of the method may include one or more of the following, in any combination.

In an embodiment, the method further includes distally advancing a drill bit through the drill guide sleeve and drilling a first hole through the first bone.

In an embodiment, the method further includes distally advancing the drill bit into contact with a second bone and drilling a second hole through the second bone, where the first and second holes are aligned along the longitudinal axis of the drill guide.

In an embodiment of the method, the first bone is a clavicle of a patient and the second bone is a coracoid process of the patient.

In an embodiment of the method, the drill guide body further includes a stabilizing member. The stabilizing member includes a first elongate portion extending distally from the guide body, where a distal end of the first portion is positioned distally with respect to the distal end of the sleeve and a second elongate portion extending from the distal end of the first portion and transversely with respect to the longitudinal axis, where the second portion of the stabilizing member intersects the longitudinal axis.

In an embodiment of the method, securing the drill guide body to the patient's anatomy further includes positioning the drill guide body on top of the patient's shoulder and placing the second portion of the stabilizing member under the patient's scapula.

In an embodiment of the method, the drill guide sleeve is not rotated while positioned within the first channel of the drill guide.

In an embodiment of the method, the drill guide further includes a ratchet mechanism. The ratchet mechanism includes a pawl mounted to the engagement member and a plurality of teeth mounted to the sleeve, where the pawl engages the plurality of teeth in the engaged position of the engagement member to inhibit proximal motion of the sleeve.

In an embodiment of the method, the drill guide body further includes a biasing mechanism positioned within the second channel, where the biasing mechanism biases the engagement member in the engaged position.

In an embodiment, the method further includes, after drilling the first and second holes, removing the drill guide body from the patient's anatomy while retaining the drill guide sleeve in place.

In an embodiment, the method further includes moving the drill guide sleeve laterally with respect to the longitudinal axis such that the locating member exerts a lateral force on the clavicle.

In an embodiment of the disclosure, a drill guide is provided. The drill guide includes a tubular guide sleeve extending along a longitudinal axis of the drill guide between a proximal end and a distal end and a drill guide body including a proximally-facing surface, a distally-facing surface, and a plurality of lateral surfaces extending therebetween. The drill guide body further includes a first channel extending through the guide body between the proximal and distal guide body surfaces and aligned with the longitudinal axis, the first channel dimensioned to receive the tubular sleeve, and a second channel extending through at least a portion of the guide body and a lateral surface of the guide body transverse to the longitudinal axis, the second channel intersecting the first channel. The drill guide also includes an engagement member dimensioned for placement within the second channel, the engagement member including a through-passageway oriented parallel to the first channel when the engagement member is positioned within the second channel, the passageway dimensioned for receipt of a portion of the sleeve therein. The engagement member is further adapted to move linearly within the second channel between an engaged position and a disengaged position, where the engagement member inhibits proximal movement of the sleeve in the engaged position, and where the engagement member does not inhibit proximal movement of the sleeve in the disengaged position.

Embodiments of the drill guide may include one or more of the following, in any combination.

In an embodiment of the drill guide, the engagement member is rotatable to move between the engaged position and the disengaged position. In an embodiment, the drill guide further includes a ratchet mechanism. The ratchet mechanism includes a pawl mounted to the engagement member and a plurality of teeth mounted to the sleeve, where the pawl engages the plurality of teeth in the engaged position of the engagement member to inhibit proximal motion of the sleeve.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1:
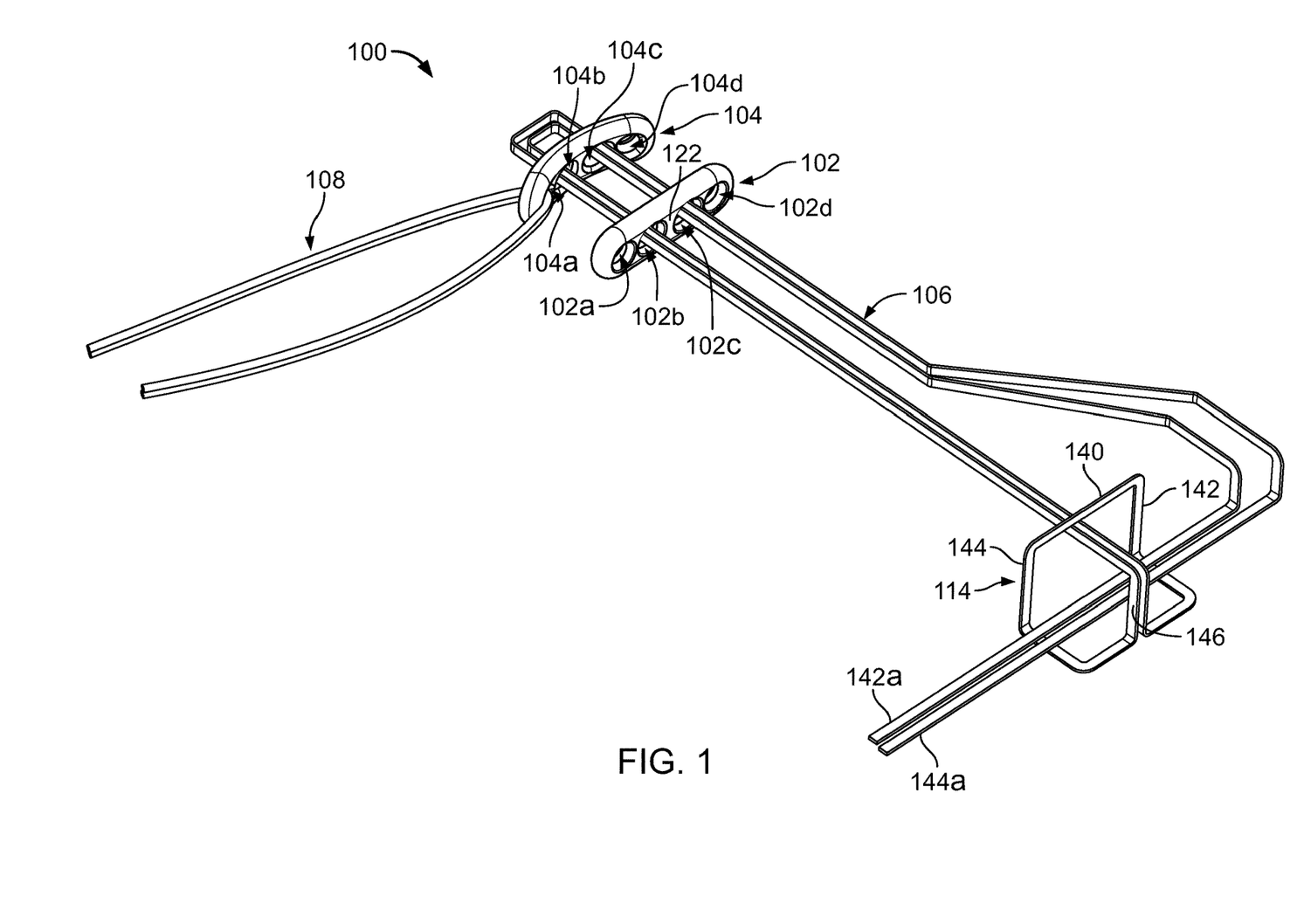
FIG. 1 is a perspective view of a surgical fastening device.

Referring to FIG. 1, a surgical fastening device 100 used, for example, in the repair of complete acromioclavicular joint and coracoclavicular ligament disruption in a patient's shoulder, includes a planar first fastener 102, a curved second fastener 104, a tension suture 106, and a lead suture 108.

Figure 2A:
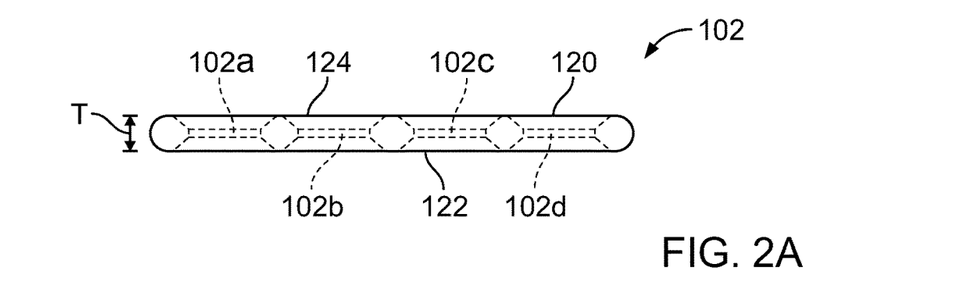
FIGS. 2A and 2B are top and side views of a first fastener of the surgical fastening device.
Figure 2B:
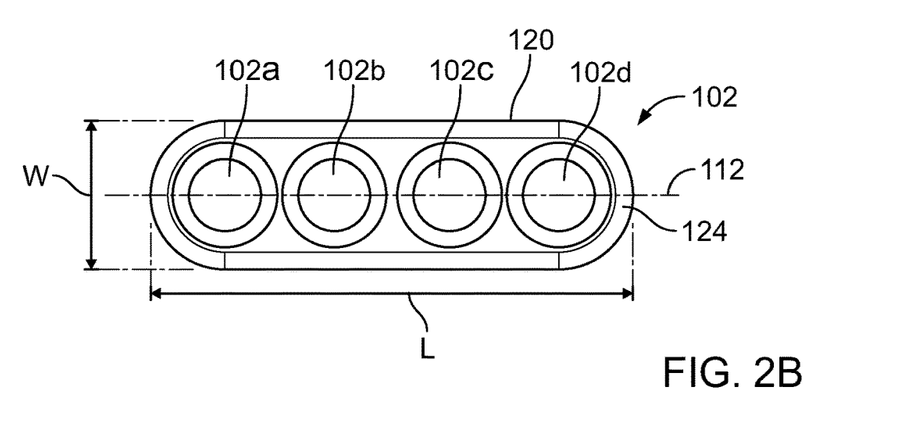
Figure 3A:
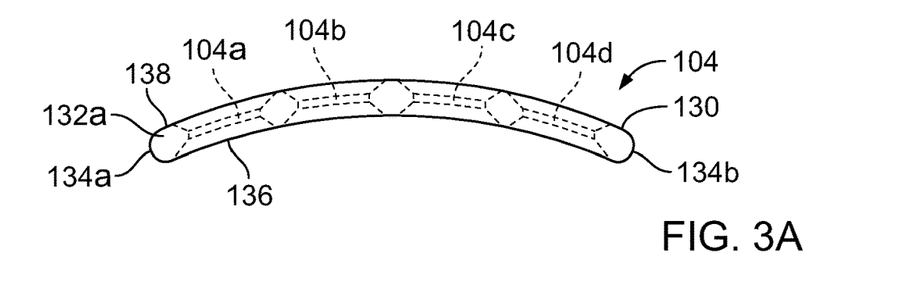
FIGS. 3A and 3B are top and side views of a second fastener of the surgical fastening device.
Figure 3B:
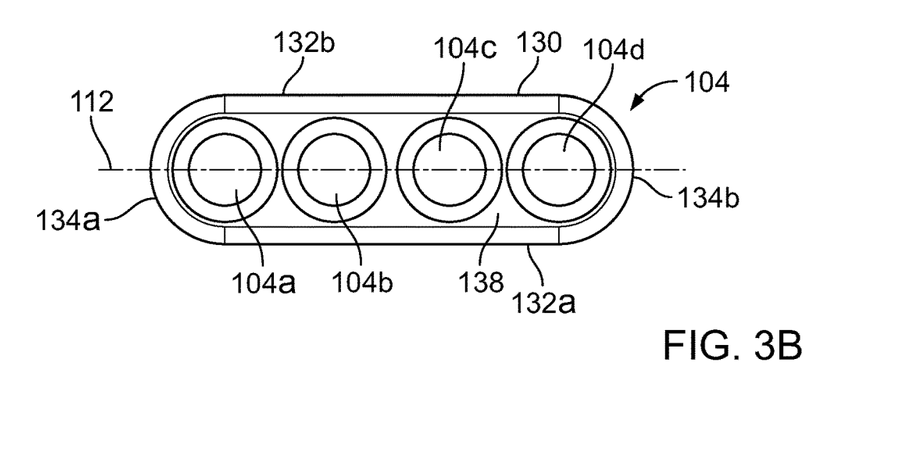

As illustrated in FIGS. 2A and 2B, the first fastener 102 has an elongate, generally rectangular fastener body 120 having a length, $L_1$, along a long axis, 112, of the fastener body of, for example, 14 mm, a width, $W_1$, of, for example, 4 mm, and a thickness, $T_1$, of, for example, 1.5 mm. However, the exact dimensions of the fastener body 120 may be varied. For example, the dimensions may be varied to accommodate a patient or procedure. The first fastener body 120 has a planar profile with a first surface 122 and a second surface 124 that are flat and parallel. The first fastener 102 defines four holes 102a, 102b, 102c, and 102d. Holes 102b and 102c receive suture 106. Alternatively, any combination of holes 102a, 102b, 102c, and 102d may receive suture 106. The second fastener 104, illustrated in FIGS. 3A and 3B, has an elongate, generally rectangular fastener body 130 having, for example, the same overall length, width, and thickness as fastener 102. The second fastener 104 has long edges 132a, 132b, short edges 134a, 134b, a first surface 136 that is concave, and a second surface 138 that is convex such that the fastener body 130 has a curved profile when viewed along a long edge 132a or 132b of the fastener body 130. The second fastener 104 defines four holes 104a, 104b, 104c, and 104d. Holes 104b, 104c receive suture 106, and hole 104a receives suture 108. Alternatively, hole 104d may receive suture 108. Moreover, any combination of holes 104a, 104b, 104c, and 104d may receive suture 106.

Tension suture 106 and lead suture 108 may be made of any common surgical suture material, including, for example, high-strength polyethylene. The tension suture 106 passes through holes 102b, 102c, 104b, and 104c and is tied off with a knot, for example a half-hitch knot 114, that allows the distance between the first fastener 102 and the second fastener 104 to be adjusted by pulling on the ends of the suture 106. The half-hitch knot 114 is formed, for example, by folding the suture 106 roughly in half to form a bight 140 with two suture lengths 142, 144, passing the suture lengths 142, 144 through the bight 140 to form a loop 146, passing the suture lengths 142, 144 through hole 102b, through hole 104b, back through hole 104c and hole 102c, and then through the loop 146. The half-hitch knot 114, also known as a Nice knot, is closed around the suture 106 and moved up to the first fastener 102 by pulling on suture ends 142a, 144a. Further pulling on the suture ends 142a, 144a shortens the length of the suture between the fasteners 102, 104, moving the fasteners closer together. When tightened, the half-hitch knot is preferably located against the first surface 122 of the fastener 102, which corresponds to an outer surface of the fastener in the assembled device 100 (FIG. 1)

Figure 4A:
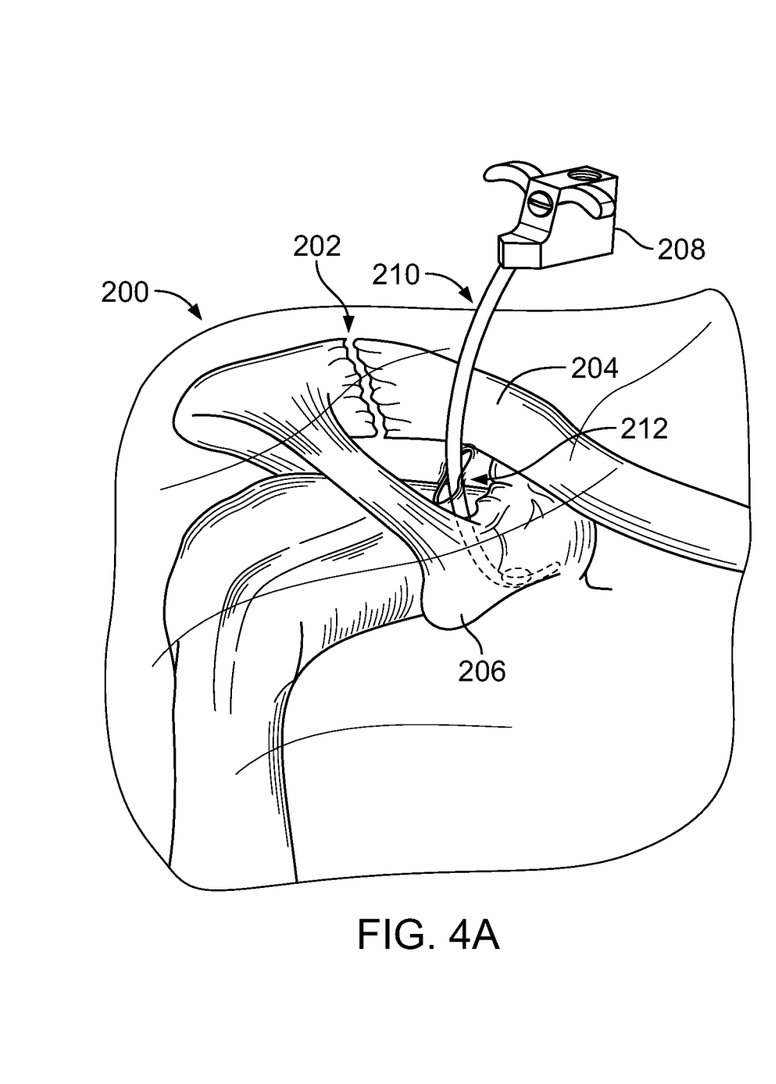
FIGS. 4A-4I illustrate a process for using the surgical fastening device of FIG. 1.
Figure 4B:
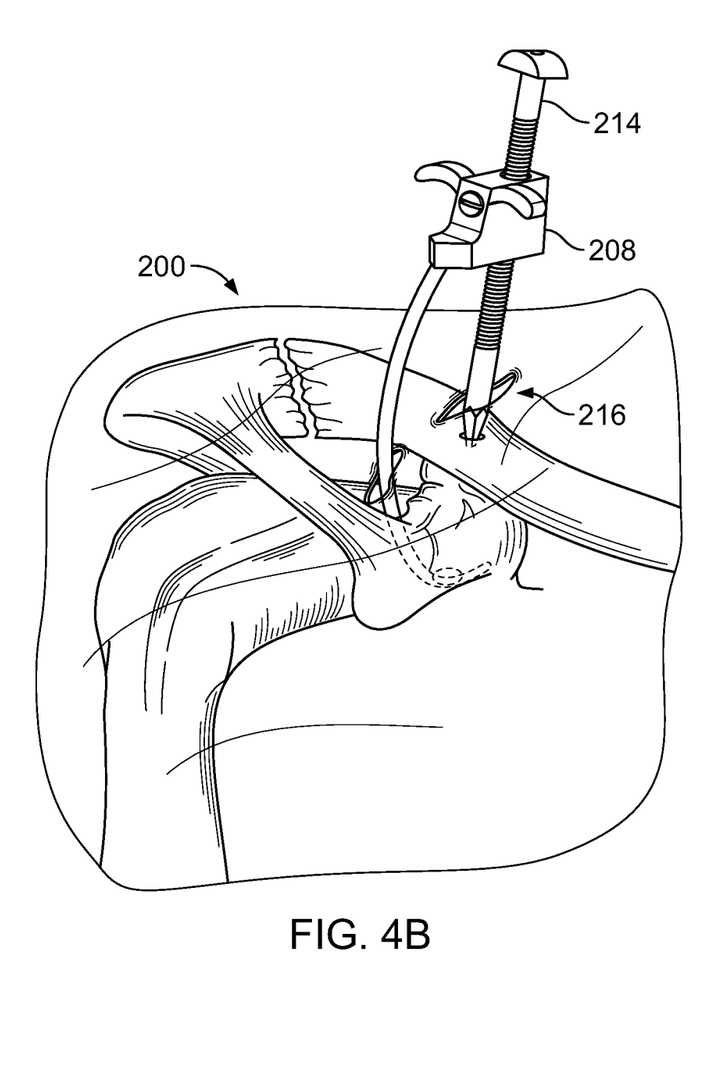

In use, referring to FIGS. 4A-4I, in which a shoulder of patient 200 is illustrated with a disrupted acromioclavicular joint 202, a clavicle 204, and a coracoid process 206, passages are initially drilled through the patient's clavicle 204 and coracoid process 206. In order to establish the passages, the patient needs to be prepared and a drilling guide secured. FIG. 4A shows a clamp 208 of a drilling guide positioned on top of the patient 200's shoulder. The clamp 208 includes a strap 210 used to secure the clamp 208 in place on the top of the patient shoulder. The strap 210 is positioned through a first portal 212 in the front of the patient 200's shoulder, under the patient's scapula, and through a second portal (not shown) in the rear of the patient's shoulder. Next, as shown in FIG. 4B, a first guide tube 214 of the drilling guide is inserted through a hole in clamp 208 and through a third portal 216.

Figure 4C:
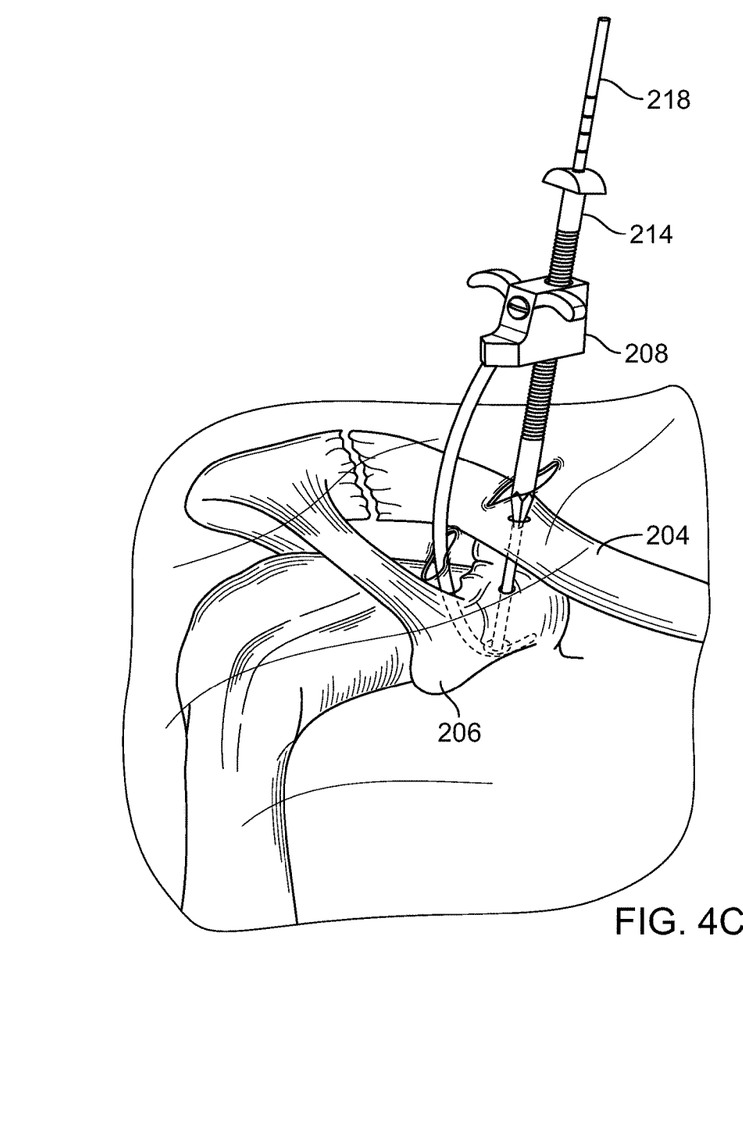
Figure 4D:
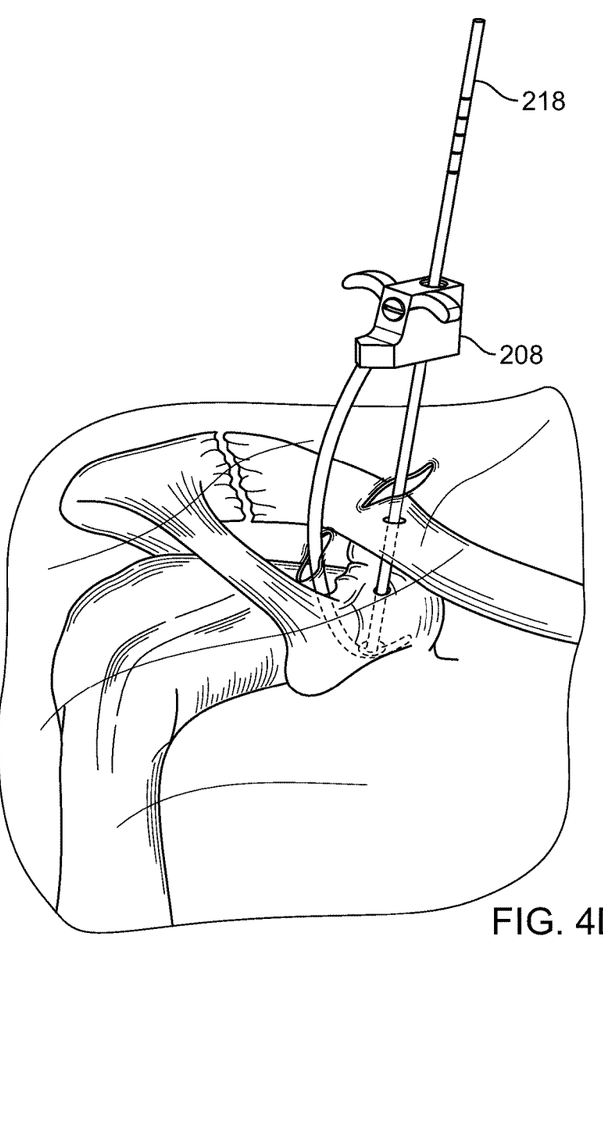
Figure 4E:
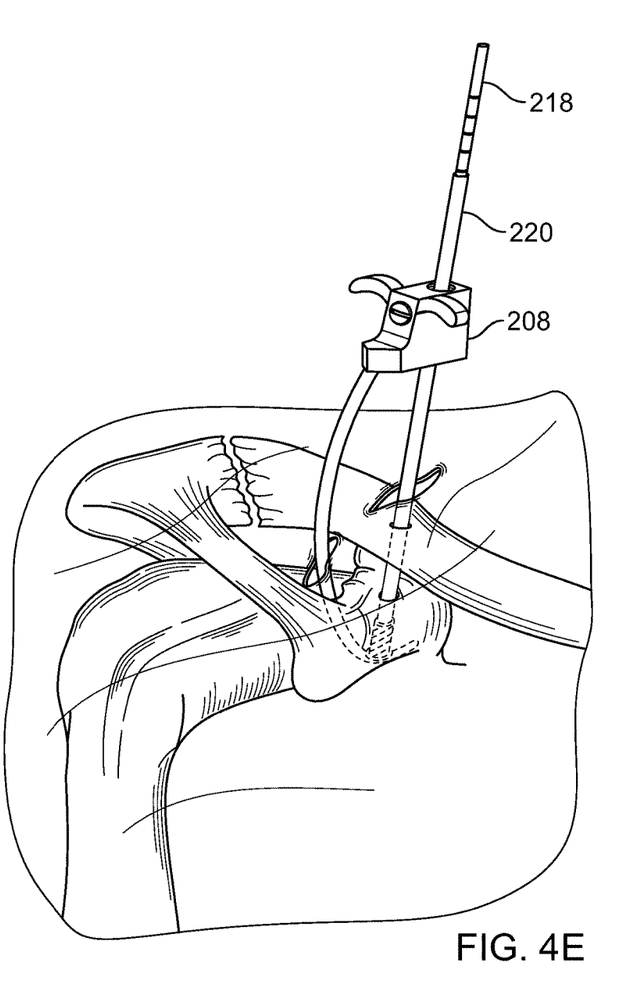

Once the drilling guide is in place, passages in the clavicle 204 and the coracoid process 206 are ready to be formed. FIG. 4C depicts a guide wire 218 (i.e., a drill bit) being inserted through a passage in the first guide tube 214. As the guide wire 218 is moved through the third portal 216 via the first guide tube 214, it encounters the clavicle 204 and is drilled through the clavicle 201 and coracoid process 206. The first guide tube 214 provides the support necessary to drill axially aligned passages through the patient's clavicle 204 and coracoid process 206. In FIG. 4D, the first guide tube 214 is removed from the clamp 208 leaving the guide wire 218 in place. The operator then advances a drill 220 over the guide wire 218 (FIG. 4E) to "over-drill" the passages through the clavicle 204 and the coracoid process 206 to form bone passages each having a diameter that is less than the length, L, of the first and second fasteners 102, 104.

Figure 4F:
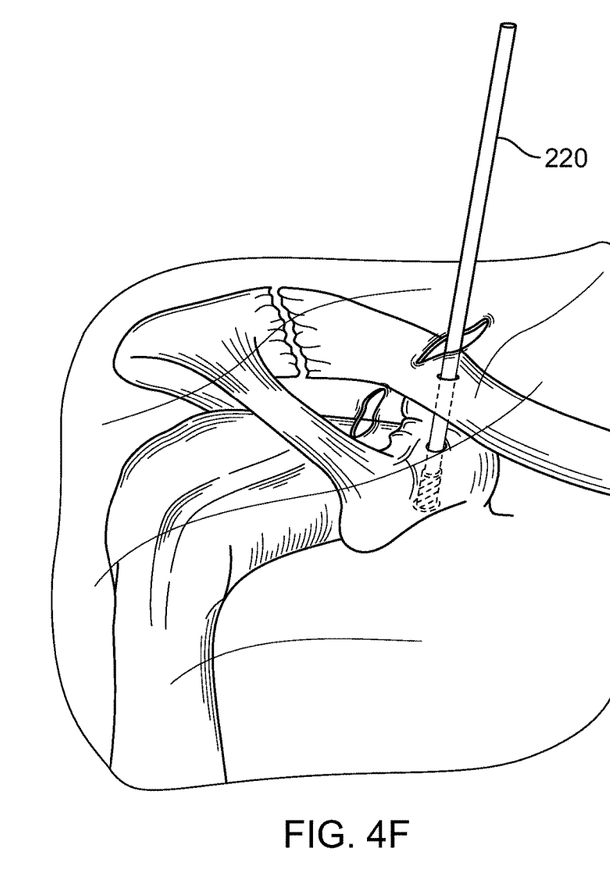
Figure 4G:
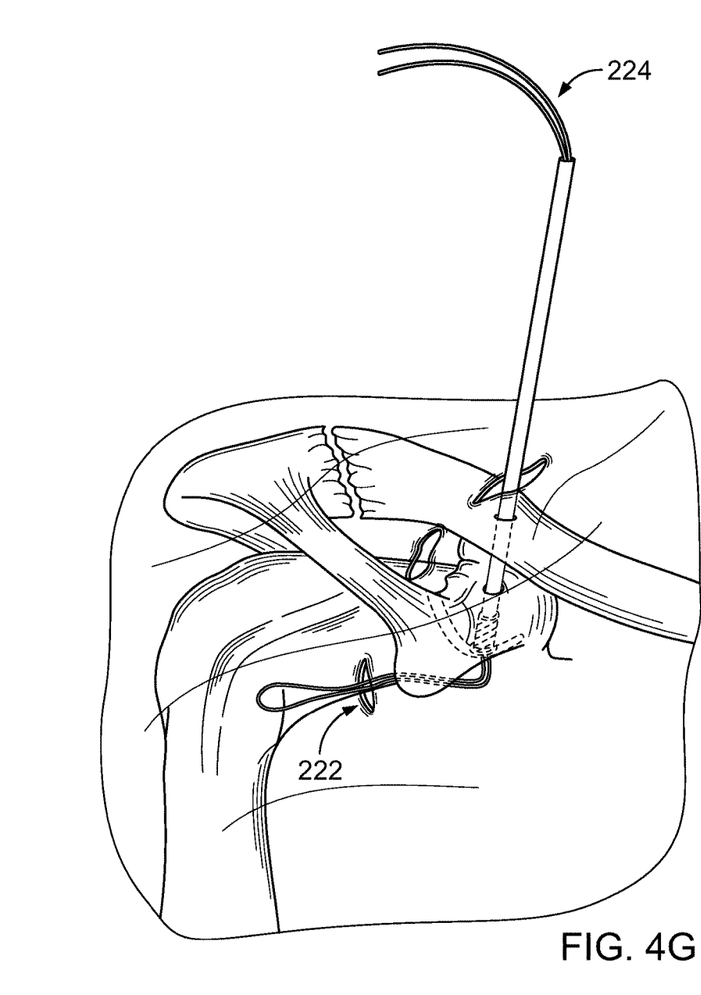

After the aligned passages through the patient's clavicle 204 and coracoid process 206 have been formed, the clamp 208 is removed from the patient's shoulder, as illustrated in FIG. 4F. However, drill 220 is left in place. At this point, the patient's shoulder is prepared for insertion of the surgical fastening device 100. Initially, as shown in FIG. 4G, a fourth portal 222 is created in the patient's shoulder. Next, a shuttling mono-suture 224 is passed through the axially aligned passages in the patient's clavicle 204 and coracoid process 206 via the drill 220.

Figure 4H:
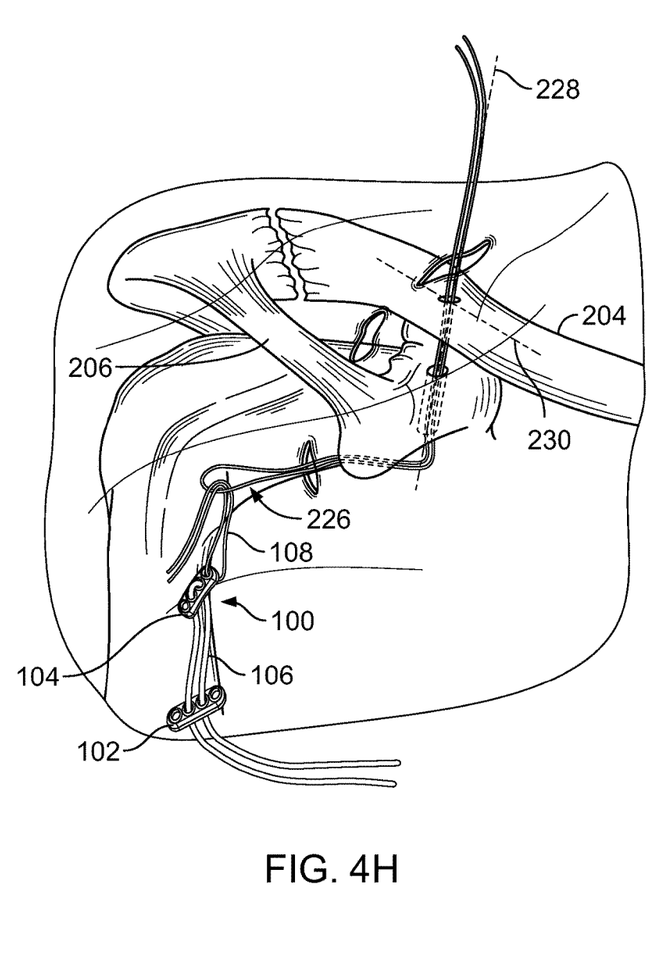
Figure 4I:
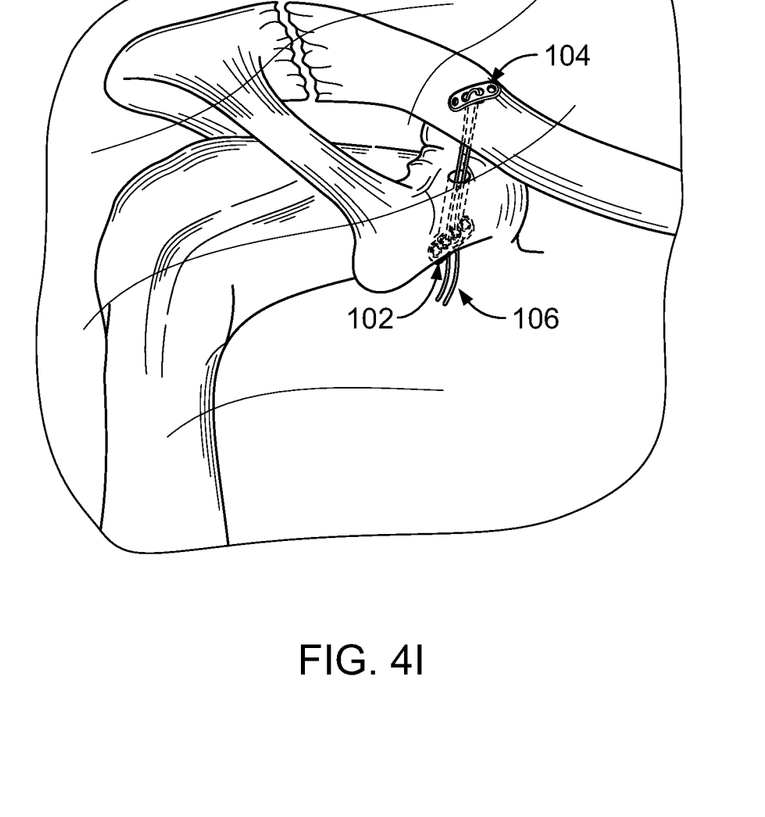

In FIG. 4H, the surgical fastening device 100 is attached to the shuttling mono-suture 224. In particular, the lead suture 108 is passed through a loop 226 in the end of the shuttling mono-suture 224. The shuttling mono-suture 224 is used to pull the surgical fastening device 100 into the patient's shoulder through the fourth portal 222. The shuttling mono-suture 224 pulls the lead suture 108, second fastener 104, and tension suture 106 up through the axially aligned passages in the patient's clavicle 204 and coracoid process 206, with the first fastener 102 and the half-hitch knot 114 positioned below the coracoid process 206 (FIG. 4I). Positioning the knot 114 below the coracoid process 206 rather than above the clavicle 204 lessons any visible protrusion of the surgical fastener on the top of the patient's shoulder and decreases the likelihood of infection.

During passage of the second fastener 104 through the passages in the patient's clavicle 204 and coracoid process 206, a long axis 112 (FIG. 3B) of the second fastener 104 is aligned with a longitudinal axis 228 of the passages. After exiting through the passage in the clavicle 204, the operator flips the second fastener 104 using the suture 108. The second fastener 104 is seated on the top surface of the clavicle 204 with the long axis 112 of the second fastener 104 roughly transverse to an axis 230 of the clavicle 204, and the concave surface 136 abutting the surface of the clavicle 204.

With the first fastener 102 positioned below the coracoid process 206, the second fastener 104 positioned above the clavicle 204, and the suture 106 extending through the passages in the coracoid process 206 and clavicle 204, the coracoclavicular is manually reduced through application of external pressure on the patient's shoulder to reduce the distance between the patient's coracoid process and clavicle to re-approximate the bones, tendons, and ligaments back to their anatomical locations.

Next, the operator pulls on the ends 142a, 144a of the suture 106 to shorten the length of the suture 106 between the fasteners 102, 104 such that the distance between the fasteners 102, 104 conforms to the reduction in the coracoclavicular, with the surface 120 of the first fastener 102 up against the surface of the coracoid process 206. The operator then further reduces the coracoclavicular if desired. After the coracoclavicular is reduced to the preferred distance, a surgical knot is tied behind the half-hitch knot 114. The shuttling mono-suture 224 is removed from the patient 200. Finally, the first portal 212, the second portal (not shown), the third portal 216, and the fourth portal 222 are stitched closed.

The passages formed in the coracoid process 206 and the clavicle 204 are sized to allow passage of the second fastener 104. Relatedly, the curvature of the second fastener 104 is selected such that the second fastener 104 can pass through the passages and to match the size and curvature of the patient's clavicle 204. For the same length fastener, as the curvature of the second fastener 104 increases, the diameter of the passages necessarily increases to allow the second fastener 104 to pass through the passages. However, it is generally better to keep the diameter of the passages formed in the coracoid process 206 and the clavicle 204 as small as possible to maintain the integrity of the coracoid process 206 and the clavicle 204. Therefore, depending on the size of the clavicle 204, there can be a trade-off between the diameter of the passages and the extent to which the curvature of the second fastener 104 matches that of the clavicle 204. To accommodate different sized patients, a kit of surgical fastening devices 100 can be provided to the surgeon, with each surgical fastening device 100 including a second member having a different curvature or varying in other different overall dimensions.

Further embodiments of fasteners are discussed in U.S. Pat. No. 8,926,661, entitled "Surgical Fastening," the entirety of which is hereby incorporated by reference.

Another embodiment of the drilling guide for use in combination with embodiments of the surgical fastening device 100 and embodiments of the repair procedure of FIGS. 4A-4I is illustrated in FIGS. 5A-5B and 6A-6B. The drill guide 500 includes a body 502, a stabilizing member or strap 504, a tubular guide sleeve or bullet 506, and an engagement member 510. By way of reference, distal and proximal will refer to relative distances, where distal represents a position closer to the patient than proximal.

The body 502 includes a proximally-facing surface, a distally-facing surface, and lateral faces extending there-between. A first channel 600 is formed through the body 502, extending between the distally- and proximally-facing surfaces and aligned with a longitudinal axis 512 of the drill guide 500. The first channel 600 (FIG. 6A) is dimensioned to receive the guide sleeve 506, as discussed in greater detail below. A second channel 602 is further formed within the body 502, extending transversely with respect to the longitudinal axis 512 from a lateral face of the body 502 and terminating therein. In certain embodiments, the second channel 602 may be approximately perpendicular to the second channel.

Figure 5A:
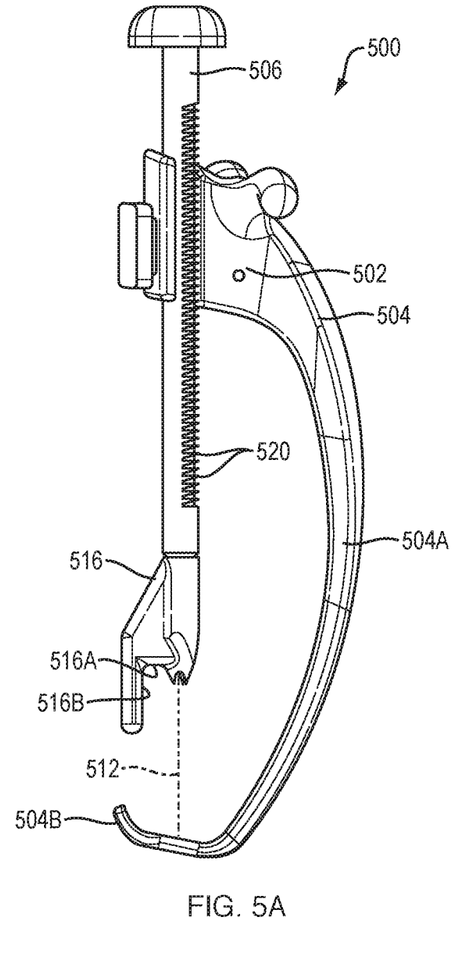
FIGS. 5A-5B are schematic illustrations of an embodiment of an improved drill guide for use in embodiments of the process of FIGS. 4A-4I; (A) side view; (B) opposing side view.
Figure 5B:
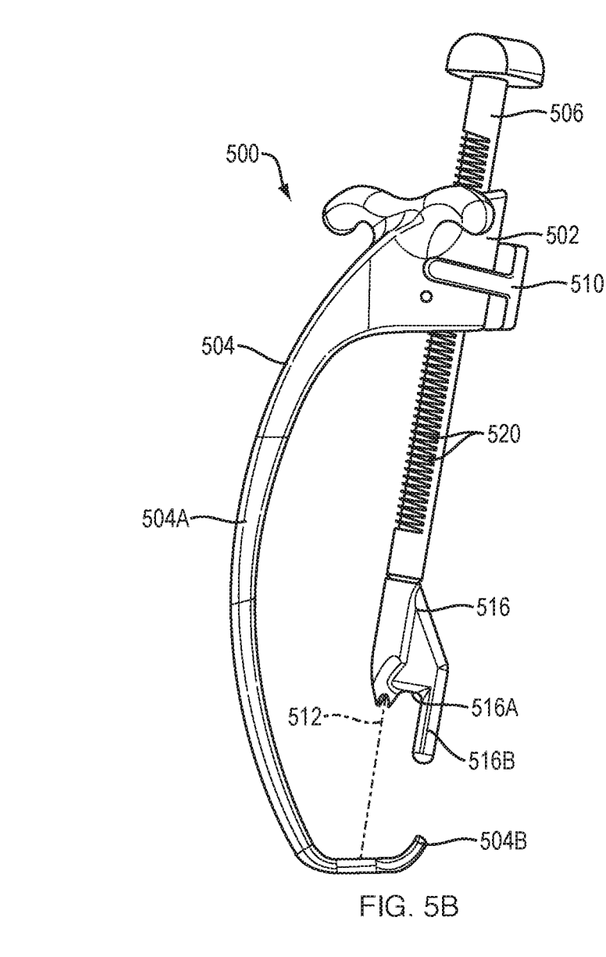

The guide sleeve 506 is generally elongated, enclosing a lumen (not shown) that extends between proximal and distal ends of the sleeve 506. The lumen may be dimensioned to accommodate a wire or drill bit (e.g., 218). The distal terminus of the sleeve 506 may be formed with a plurality of sharp points, for use in engaging bone when the sleeve 506 is positioned. The sleeve 506 may further include a plurality of teeth 520 on its outer surface for mechanically engaging the engagement member 510, as discussed in greater detail below.

The guide sleeve 506 further includes an alignment member 516 positioned at the distal end of the sleeve 506. The alignment member 516 may be mounted to the sleeve 506 or integrally formed with the sleeve 506. The alignment member 516 may include a distally-facing surface 516A and a generally elongated locating member or finger 516B. The locating member 516B is mounted to the distally-facing surface 516A at a distance laterally spaced from the guide sleeve 506 and extends distally from the distally-facing surface 516A. In certain embodiments, the locating member 516A may be dimensioned such that its distal terminus extends distally beyond the distal terminus of the guide sleeve 506. In further embodiments, the distally-facing surface 516A and the locating member 516B may be formed at an approximately right-angle. In further embodiments, the locating member 516B may be oriented approximately parallel to guide sleeve 506 and/or the longitudinal axis 512 of the guide 500.

It may be understood, however, that in alternative embodiments, the locating member and/or the distally facing surface may be further adapted for adjustable placement with respect to the guide sleeve 506 and/or the longitudinal axis 512 of the drill guide 500. For example, either or both of the locating member and the distally facing surface may include one or more pivot points for adjustment of their positions. Alternatively, or additionally, either one or both of the locating member and the distally facing surface may be formed from a plastically deformable material for adjustment of their positions.

The stabilizing member 504 is generally elongated, mounted to the guide body 502 and extending distally there-from. The stabilizing member 504 may include a first elongated portion 504A and a second portion 504B. The first stabilizing member portion 504A may extend distally from the guide body 502 and be dimensioned to extend beyond the distal terminus of the guide sleeve 506. In certain embodiments, the first stabilizing member portion 504A may be curved. The second stabilizing member portion 504B may extend transversely from the distal end of the first stabilizing member portion 504A and intersecting the longitudinal axis 512. The second stabilizing member portion 504B may further include a planar portion which functions as a physical barrier or stop for a drill bit traveling through the sleeve 506.

With further reference to FIGS. 6A-6B and 7A-7B, the engagement member 510 is illustrated. The engagement member 510 is generally elongate, having a first portion 510A and a second portion 510B. The first portion of the engagement member 510A is dimensioned for receipt and reversible sliding within the second channel 602. While inserted within the second channel 602, the second portion of the engagement member 510B remains outside the guide body 502.

Figure 6A:
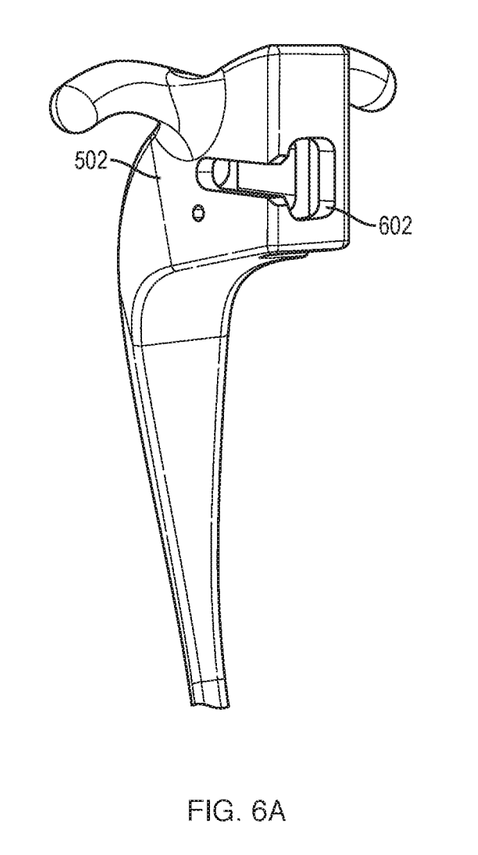
FIGS. 6A-6B are schematic illustrations of an embodiment of the drill guide of FIGS. 5A-5B in a magnified view highlighting the drill guide body.
Figure 6B:
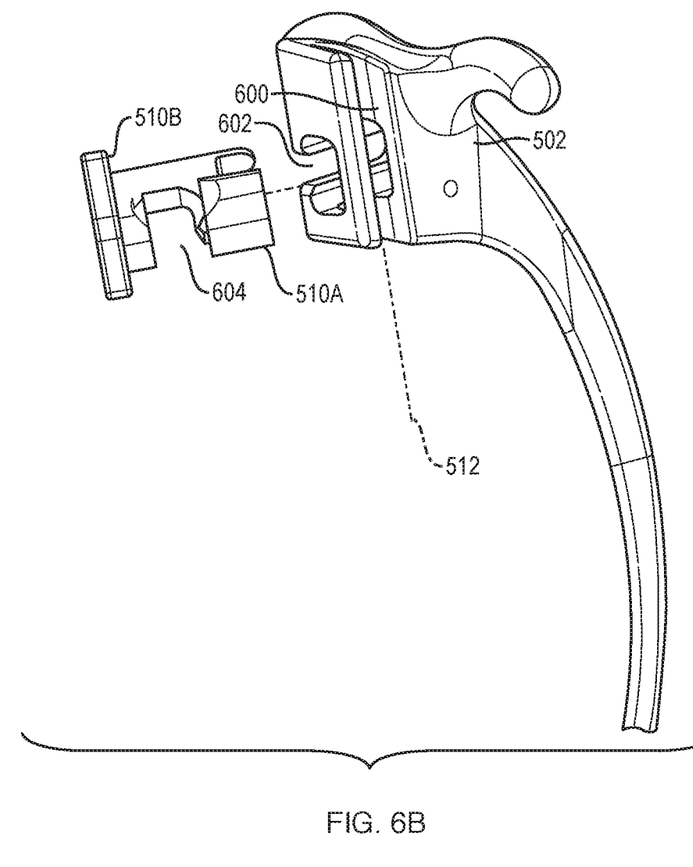

The first portion of the engagement member 510A further includes a through passageway 604 dimensioned to receive a portion of the guide sleeve 506 (e.g., a portion of the sleeve 506 proximal to the alignment member 516. When inserted a selected distance within the second channel 602 of the guide body 502, the passageway 604 is axially aligned with the first channel 600.

Figure 7A:
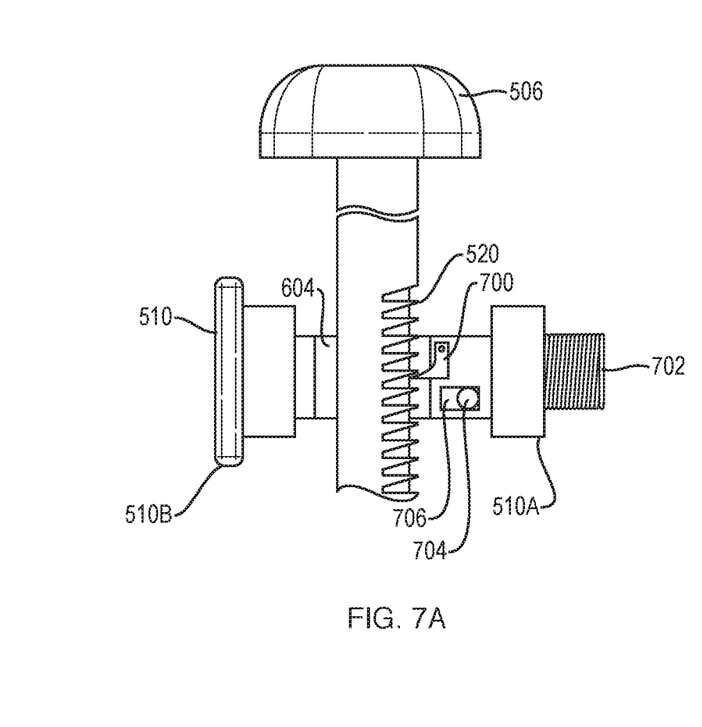
FIGS. 7A-7B are schematic illustrations of an engagement mechanism for reversibly securing a guide sleeve of the drill guide; (A) front view; (B) rear view.
Figure 7B:
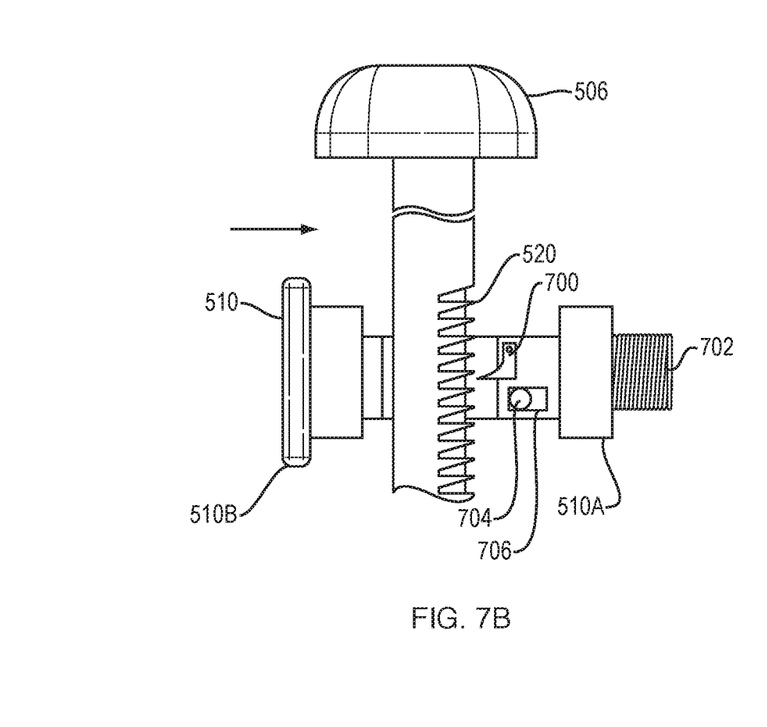

As illustrated in FIGS. 7A-7B, the engagement member 510 may be actuated by a user to reversibly slide the engagement member 510 within the second channel 602 between an engaged position and a disengaged position. For example, in the engaged position (FIG. 7A), proximal movement of the guide sleeve 504 may be inhibited, while distal movement of the guide sleeve 504 may be permitted. Furthermore, in the disengaged position (FIG. 7B), proximal or distal movement of the guide sleeve 506 may be allowed. Beneficially, the constraint provided by the engagement member 510 may allow a surgeon the confidence of distally advancing the sleeve 506 within the guide body 502 while the engagement member 510 is in the engaged position without concern of accidental proximal retraction of the sleeve 506. Subsequently, placing the engagement member 510 intentionally in the disengaged position, the surgeon may remove the guide sleeve 506 from the drill guide body 502.

In certain embodiments, the constraint provided in the engaged position may be achieved by a ratcheting mechanism formed within the engagement member 510 and the guide sleeve 506. For example, with further reference to FIGS. 7A, 7B, the ratcheting mechanism includes a pawl 700 mounted to the engagement member 510 and the teeth 520 of the guide 506. In the engaged position (e.g., the pawl 700 engages the teeth 502 of the guide sleeve 506 (FIG. 7A). As a result, proximal motion of the guide sleeve 506 is inhibited, while distal motion of the guide sleeve 506 is allowed. Sliding the engagement member 510 within the second channel 602 such that the pawl 700 does not engage the teeth 502 moves the engagement member 510 into the disengaged position (FIG. 7B). As a result, the guide sleeve 506 is free to move either proximally or distally.

The engagement member 510 may be further biased in the engaged position in order to decrease the likelihood that it is positioned in the disengaged position accidentally. For example, a biasing member 702 may be positioned within the second channel 602. The biasing member 702 exerts a biasing force upon the engagement member 510, urging the engagement member 510 into the engaged position absent actuation by the user in a direction opposite this bias. In an embodiment, the biasing member 702 may be a spring. However, other biasing mechanisms may be employed without limit.

In order to limit travel of the engagement member 510 within the second channel 602 between the engaged and disengaged positions, the drill guide 500 may further include a limiting mechanism. For example, the limiting mechanism may include a pin 704 extending outward from the engagement member 510 and a slot 706 formed in the second channel 602. Travel of the engagement member 510 within the second channel 602 may be limited within the length of the slot 706. For example, when in the engaged position, the pin 702 may abut one end of the slot 704, while in the disengaged position, the pin 702 may abut the opposing end of the slot 704. Beneficially, with this configuration, the engagement member 510 is inhibited from contacting the guide sleeve 506 with sufficient force to damage any of the ratchet mechanism, the guide sleeve 506, or the engagement member 510.

Figure 8A:
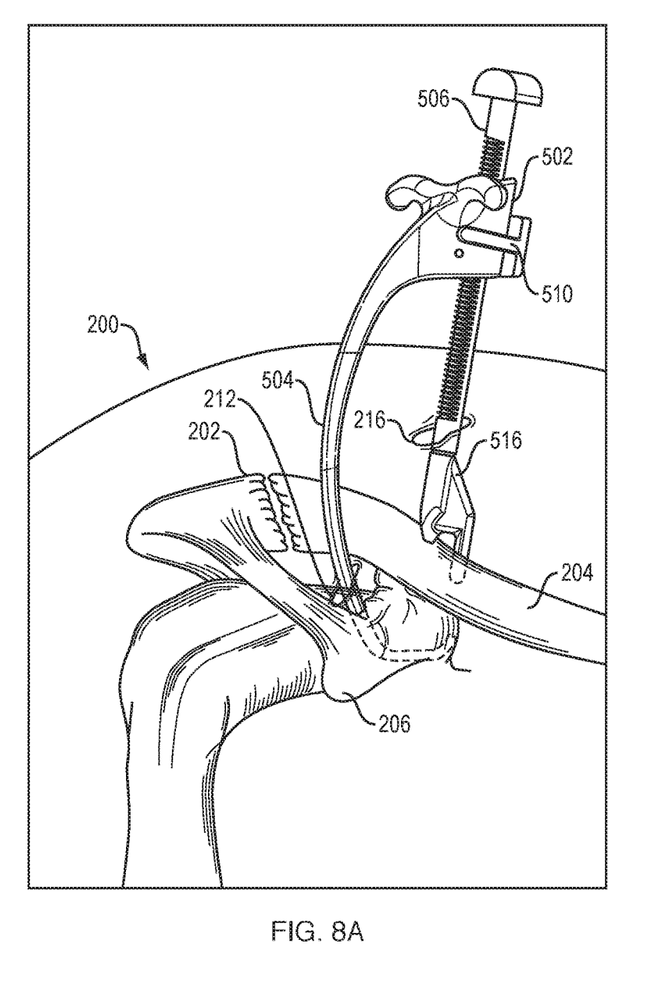
FIGS. 8A-8B are schematic illustrations of an embodiment of the drill guide of FIGS. 5A-5B positioned on a patient's clavicle; (A) overall; (B) magnified region of clavicle.
Figure 8B:
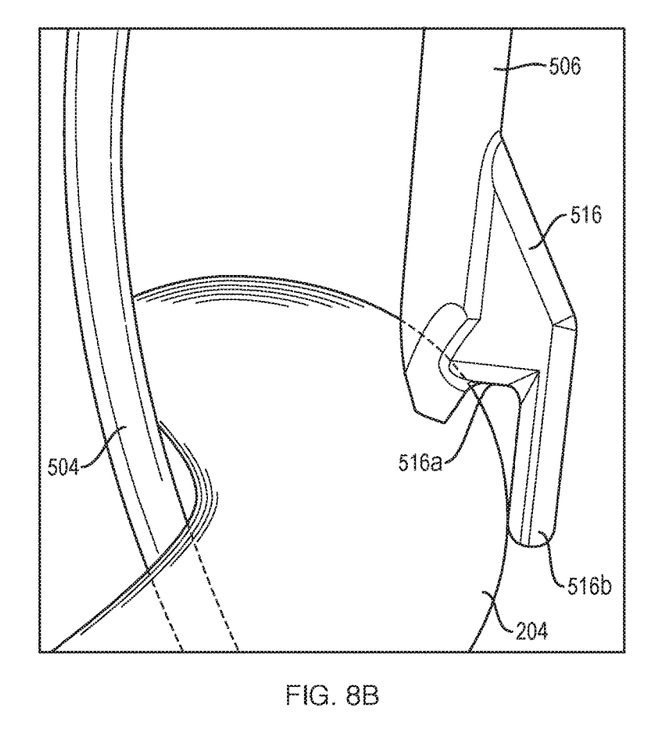

The discussion will now turn to FIGS. 8A-8D, which illustrate positioning of the drill guide 500 in a surgical operation. The drill guide 500 may generally be employed in a surgical operation to repair a disrupted acromioclavicular joint 202, including a clavicle 204 and a coracoid process 206, as discussed above with respect to FIGS. 4A-4I. For example, as illustrated in FIG. 8A, the drill guide body 502 is positioned on top of the patient's shoulder 200, where the stabilizing member 504 is used to secure the drill guide body 502 in place. The stabilizing member 504 may be positioned through the first portal 212 in the front of the patient's shoulder 200, under the patient's scapula, and through a second portal (not shown) in the rear of the patient's shoulder. Next, the guide sleeve 506 of the drill guide 500 is inserted through the first channel 600 in the guide body 502, and through the third portal 216. The sleeve 506 is advanced distally (e.g., with the engagement member 510 in the engaged position) such that the distal end of the guide sleeve 506 contacts a proximally facing surface of the clavicle 204.

Figure 8C:
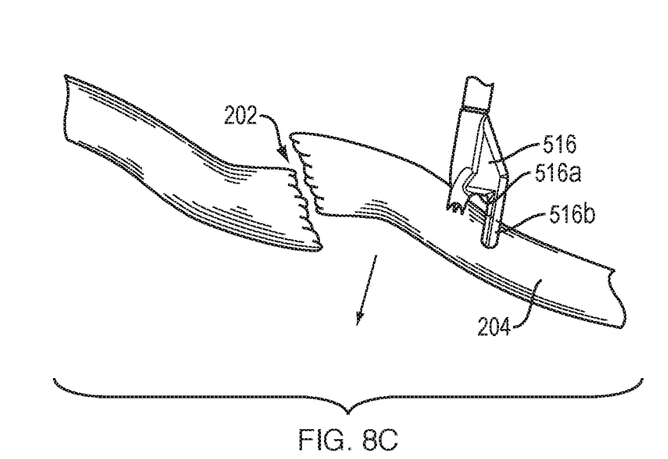
FIGS. 8C-8D are schematic illustrations of an embodiment of the drill guide of FIGS. 5A-5B on a patient's clavicle highlighting use of the drill guide for positioning the clavicle.
Figure 8D:
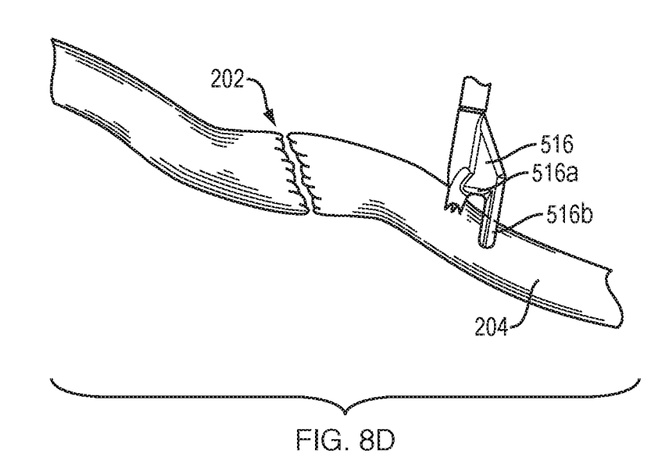

Notably, in addition to the operations discussed above with respect to FIGS. 4A-4I, the drill guide 500 may also be positioned such that the alignment member 516 abuts the clavicle 204. For example, the distal end of the sleeve 506 may be advanced distally to contact a position on the proximally-facing surface of the clavicle 204 such that at least a portion of the locating member 516B contacts a laterally-facing surface of the clavicle 216. In this position, the alignment member 516 may be moved laterally with respect to the longitudinal axis 512 such that the locating member 516B exerts a lateral force on the clavicle 204. Beneficially, application of such lateral forces may allow the clavicle 204 and/or the acromioclavicular joint 202 to be repositioned in an arrangement more suitable for repair, as illustrated in FIGS. 8C-8D.

While discussed above with respect to AC joint repair, it may be understood that embodiments of the drill guide 500 may be employed in other joint and/or bone repair procedures as well.

Figure 9A:
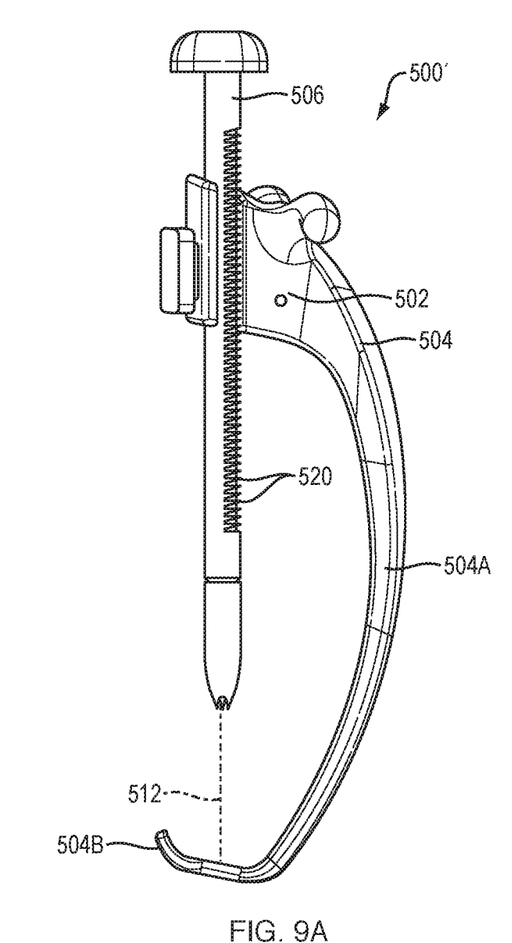
FIGS. 9A-9B are schematic illustrations of another embodiment of the improved drill guide.
Figure 9B:
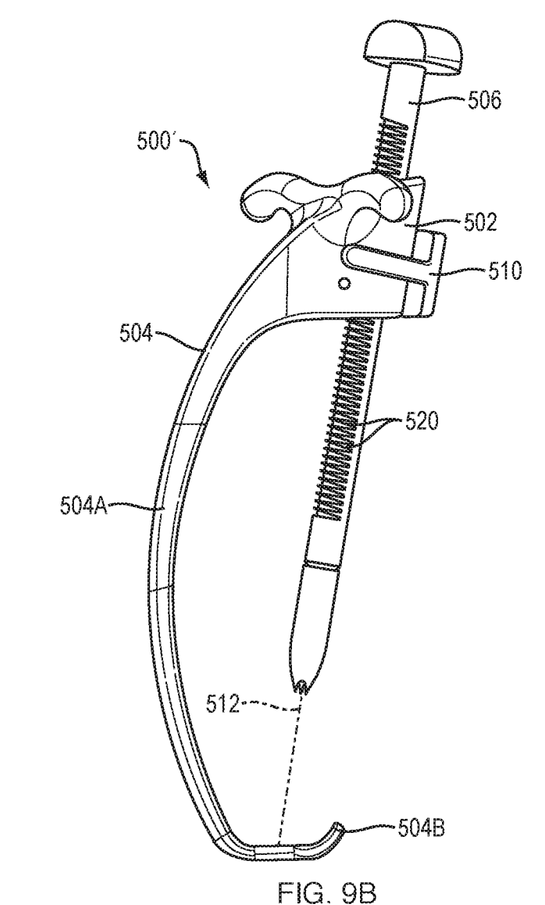

In alternative embodiments, a drill guide 500' may be provided, as illustrated in FIGS. 9A-9B. The guide 500' is identical to guide 500 except that the alignment member 516 is omitted from the sleeve 506. This configuration may be advantageous for use in joint repairs where it desirable to proximally retract the guide sleeve 506 from the guide body 502 after use (e.g., after contact with joint 202). Notably, injured joints can be particularly susceptible to destabilization due to forces applied during repair operations. However, the ability to withdraw the guide sleeve 506 of guide 500' from a joint space without rotating or transversely sliding the guide sleeve 506 can mitigate this issue.

The terms comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:
1. A drill guide, comprising:
a tubular guide sleeve extending along a longitudinal axis of the drill guide between a proximal end and a distal end;
a drill guide body including a proximally-facing surface, a distally-facing surface, and a plurality of lateral surfaces extending therebetween, the drill guide body further including:
a first channel extending through the guide body between the proximal and distal guide body surfaces and aligned with the longitudinal axis, the first channel dimensioned to receive the tubular sleeve; and
a second channel extending through at least a portion of the guide body and a lateral surface of the guide body transverse to the longitudinal axis, the second channel intersecting the first channel;
an alignment member attached to the distal end of the sleeve, the alignment member including:
a distally facing surface; and
an elongated locating member extending distally from the alignment member, wherein the locating member is laterally spaced from the guide sleeve by the distally facing surface, wherein a distal end of the locating member extends distally beyond the distal tip of the sleeve;

an engagement member dimensioned for placement within the second channel, the engagement member including a through-passageway oriented parallel to the first channel when the engagement member is positioned within the second channel, the passageway dimensioned for receipt of a portion of the sleeve therein; the engagement member being further adapted to move within the second channel between an engaged position and a disengaged position, wherein the engagement member inhibits proximal movement of the sleeve in the engaged position, and wherein the engagement member does not inhibit proximal movement of the sleeve in the disengaged position.

2. The drill guide of claim 1, wherein the second passageway is approximately perpendicular to the first passageway.

3. The drill guide of claim 1, further comprising a ratchet mechanism including:
- a pawl mounted to the engagement member; and
- a plurality of teeth mounted to the sleeve;
- wherein the pawl engages the plurality of teeth in the engaged position of the engagement member to inhibit proximal motion of the sleeve.

4. The drill guide of claim 1, further comprising a biasing mechanism positioned within the second channel, wherein the biasing mechanism biases the engagement member in the engaged position.

5. The drill guide of claim 1, further comprising a stabilizing member including:
- a first elongated portion extending distally from the guide body, wherein a distal end of the first portion is positioned distally with respect to the distal end of the sleeve; and
- a second elongated portion extending from the distal end of the first portion and transversely with respect to the longitudinal axis;
- wherein the second portion of the stabilizing member intersects the longitudinal axis.

6. The drill guide of claim 1, wherein the locating member extends approximately parallel to the sleeve.

7. A drill guide, comprising:
- a tubular guide sleeve extending along a longitudinal axis of the drill guide between a proximal end and a distal end;
- a drill guide body including a proximally-facing surface, a distally-facing surface, and a plurality of lateral surfaces extending therebetween, the drill guide body further including:
  - a first channel extending through the guide body between the proximal and distal guide body surfaces and aligned with the longitudinal axis, the first channel dimensioned to receive the tubular sleeve; and
  - a second channel extending through at least a portion of the guide body and a lateral surface of the guide body transverse to the longitudinal axis, the second channel intersecting the first channel;
- an engagement member dimensioned for placement within the second channel, the engagement member including a through-passageway oriented parallel to the first channel when the engagement member is positioned within the second channel, the passageway dimensioned for receipt of a portion of the sleeve therein; the engagement member being further adapted to move linearly within the second channel between an engaged position and a disengaged position,
- wherein the engagement member inhibits proximal movement of the sleeve in the engaged position, and
- wherein the engagement member does not inhibit proximal movement of the sleeve in the disengaged position.

8. The drill guide of claim 7, wherein the engagement member is not rotatable to move between the engaged position and the disengaged position.

9. The drill guide of claim 7, further comprising a ratchet mechanism including:
- a pawl mounted to the engagement member; and
- a plurality of teeth mounted to the sleeve;
- wherein the pawl engages the plurality of teeth in the engaged position of the engagement member to inhibit proximal motion of the sleeve.

10. The drill guide of claim 7, further comprising a stabilizing member including:
- a first elongated portion extending distally from the guide body, wherein a distal end of the first portion is positioned distally with respect to the distal end of the sleeve; and
- a second elongated portion extending from the distal end of the first portion and transversely with respect to the longitudinal axis;
- wherein the second portion of the stabilizing member intersects the longitudinal axis.

* * * * *